(12) United States Patent
Doan et al.

(10) Patent No.: US 6,819,959 B1
(45) Date of Patent: Nov. 16, 2004

(54) EXTENDABLE/RETRACTABLE SCREW-IN TIP DESIGN WITH AN IMPROVED THREAD/SCREW MECHANISM

(75) Inventors: Phong D. Doan, Stevenson Ranch, CA (US); Benedict L. Gomperz, North Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 413 days.

(21) Appl. No.: 09/996,854

(22) Filed: Nov. 21, 2001

(51) Int. Cl.[7] ............................................... A61N 1/05
(52) U.S. Cl. ..................................................... 607/127
(58) Field of Search ................................ 607/115, 116, 607/119, 120, 122, 123, 126, 127

(56) References Cited

U.S. PATENT DOCUMENTS

| | | | | |
|---|---|---|---|---|
| 4,624,265 A | * | 11/1986 | Grassi | 607/123 |
| 5,020,545 A | * | 6/1991 | Soukup | 607/127 |
| 5,300,108 A | * | 4/1994 | Rebell et al. | 607/127 |
| 5,447,533 A | | 9/1995 | Vachon et al. | 607/120 |
| 5,531,780 A | | 7/1996 | Vachon | 607/120 |
| 5,649,975 A | | 7/1997 | Lindgren et al. | 607/126 |
| 5,833,715 A | | 11/1998 | Vachon et al. | 607/120 |
| 6,463,334 B1 | * | 10/2002 | Flynn et al. | 607/127 |
| 6,687,550 B1 | * | 2/2004 | Doan | 607/127 |

FOREIGN PATENT DOCUMENTS

WO    WO 97/34408    9/1997

* cited by examiner

*Primary Examiner*—Kennedy Schaetzle
*Assistant Examiner*—Kristen Droesch

(57) ABSTRACT

An implantable endocardial lead for use with a cardiac stimulation device includes an electrically active housing including a tubular end region extending to a terminal rim at the distal end of the lead and an electrical conductor within the lead extending between proximal and distal ends. An active fixation electrode within and spaced from the electrically active housing includes an electrically active helix coaxial with the endocardial lead coupled to the distal end of the electrical conductor and movable between a retracted position fully within the housing and an extended position advanced beyond the terminal rim of the housing for effecting penetration into the myocardial tissue. A guide system located proximally of the active fixation electrode serves to rotate the electrically active helix about the longitudinal axis as the helix is moved between the retracted and extended positions.

20 Claims, 6 Drawing Sheets

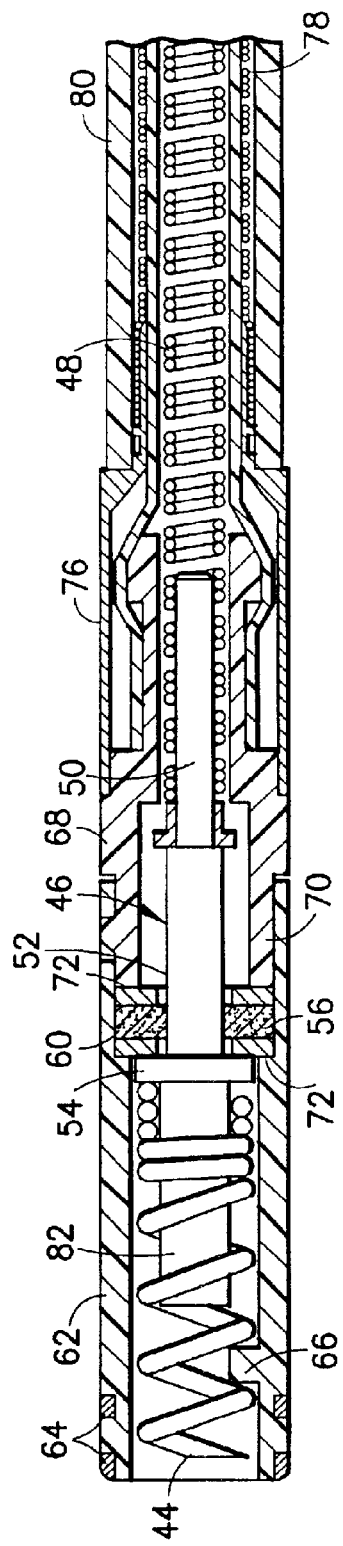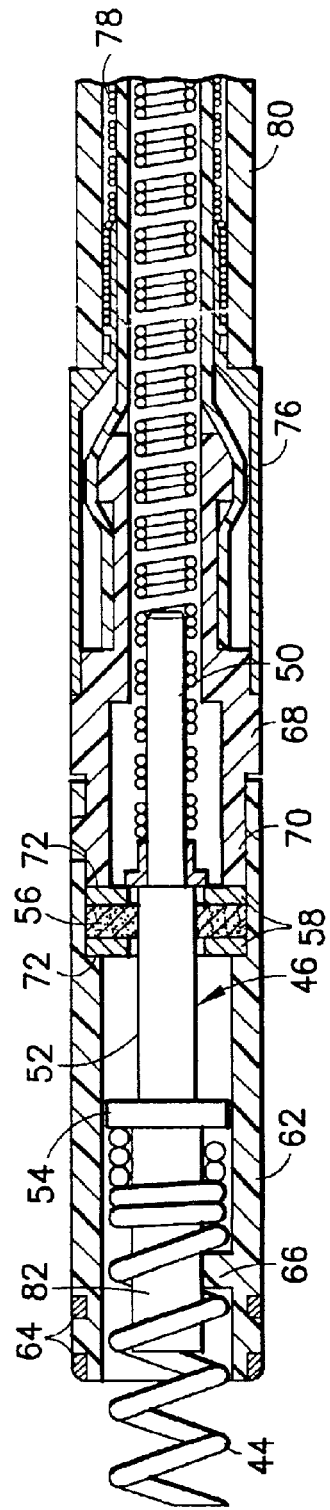

EXTENDABLE/RETRACTABLE SCREW-IN TIP DESIGN WITH AN IMPROVED THREAD/SCREW MECHANISM

FIELD OF THE INVENTION

The present invention relates generally to an implantable stimulation lead for use with an implantable pulse generator such as a cardiac pacemaker and, more specifically to such an implantable stimulation lead with the capability of selectively anchoring an electrically active helix electrode at a desired site when the lead is fixated in the heart, then withdrawing the electrode from the site.

BACKGROUND OF THE INVENTION

Currently, known extendable/retractable screw-in implantable stimulation leads have an electrically active helix electrode. The helix electrode is electrically active and is capable of extension and retraction from the header by being directly connected to the connector pin/distal coil subassembly. Turning of the connector pin results in the extension or retraction of the helix electrode from the header. In order for the helix to be extended or retracted, a thread/screw mechanism is required. The helix electrode is used as a threaded screw which turns against a thread post in the header. As the helix rotates, by turning of the connector pin, it engages the thread post, which in turn drives the helix into and out of the header. This thread/screw mechanism works smoothly when the helix electrode is straight and undamaged. However, the helix is susceptible to deformation due to its "delicate" strength and mishandling during assembly processes. A deformed or damaged helix will not only cause undesirable "sticky" or "jumpy" helix movement during the extension/retraction operation, but it may also disable the thread/screw mechanism. In addition, the thread/screw mechanism may be jammed by heart tissues that may become trapped inside the header.

Typical of the known prior art are commonly assigned U.S. Pat. Nos. 5,447,533 to Vachon et al.; 5,531,780 to Vachon; 5,649,975 to Lindegren et al.; and 5,833,715 to Vachon et al., each of which discloses an active helix electrode system employed with an implantable stimulation lead.

It was in light of the foregoing that the present invention was conceived and has now been reduced to practice.

SUMMARY OF THE INVENTION

An implantable endocardial lead for use with a cardiac stimulation device includes an electrical conductor whose proximal end is coupled to an electrical connector. An active fixation electrode is coupled to the distal end of the conductor, being movable between a retracted position fully within the lead and an extended position advanced beyond the distal end of the lead for effecting penetration into the myocardial tissue. The lead includes an electrically active housing including a tubular end region extending to a terminal rim at the distal end of the lead and an electrical conductor within the lead extends between proximal and distal ends. The active fixation electrode is located within and spaced from the electrically active housing and includes an electrically active helix coaxial with the endocardial lead coupled to the distal end of the electrical conductor and movable between a retracted position fully within the housing and an extended position advanced beyond the terminal rim of the housing for effecting penetration into the myocardial tissue. A guide system located proximally of the active fixation electrode serves to rotate the electrically active helix about the longitudinal axis as the helix is moved between the retracted and extended positions.

In the new thread/screw mechanism for the extendable/retractable helix of a screw-in lead, contrasting with the prior art, the helix electrode is no longer used as part of the thread/screw mechanism. In one embodiment, the thread/screw mechanism is relocated to the back of the header. A spiral groove creating the thread is integrated onto the header. A thread post is mounted onto the stopper. The combination of the stopper and the header provides the thread/screw mechanism for helix extension/retraction. The spiral groove of the header and the thread post of the stopper are both more robust and stronger than the combination helix electrode and header thread post. Potential helix jamming problems due to the heart tissue entrapment are also minimized since the thread/screw mechanism is located in the back end of the header where it is isolated from tissue. The functional improvements resulting from this new design provides a reliable thread/screw mechanism.

Other and further features, advantages, and benefits will become apparent in the following description taken in conjunction with the following drawings. The accompanying drawings illustrate exemplary embodiments together with the description. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 2. is a longitudinal cross section view of a known electrode assembly at the distal end of the pacing lead illustrated in FIG. 1, with the helical electrode in the retracted position;

FIG. 3, is a longitudinal cross section view of the known electrode assembly at the distal end of the pacing lead illustrated in FIG. 1, with the helical electrode in the extended position;

DETAILED DESCRIPTION OF THE PREFERRED EMBODIMENTS

Figure 1:
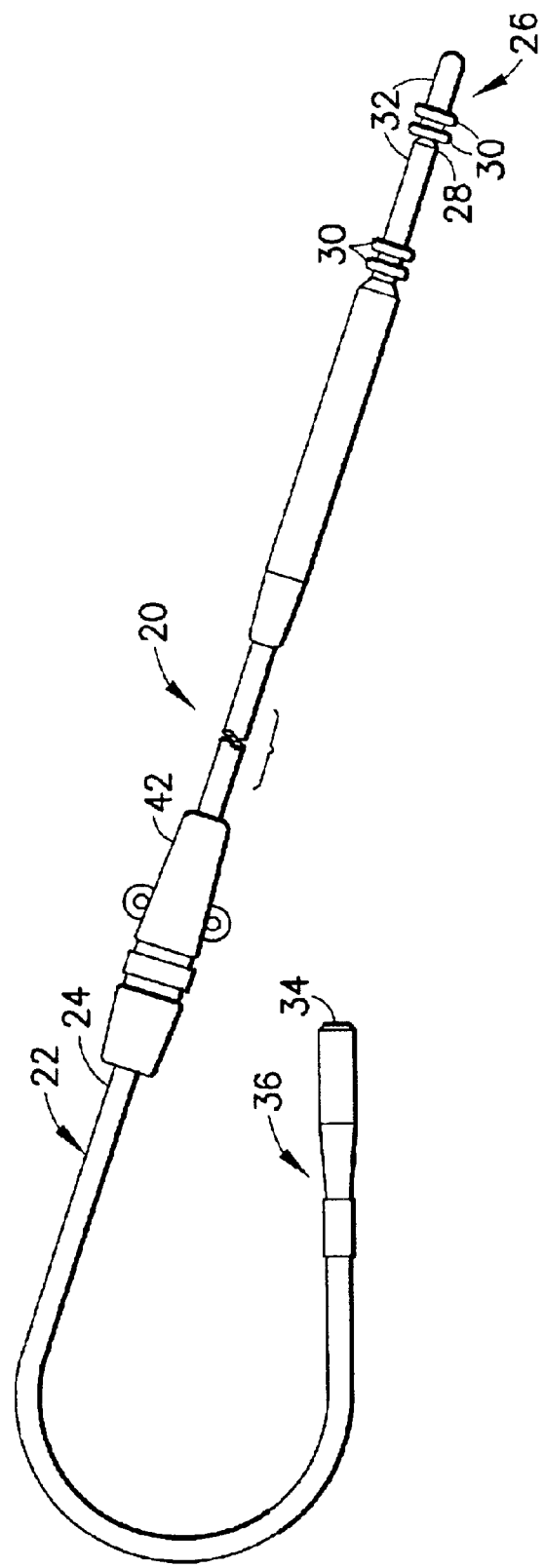
FIG. 1. is a side elevation view of a pacing lead of the type which can employ the present invention.

Turn now to the drawings and, initially to FIG. 1 which generally illustrates a perspective view of an implantable endocardial lead 20 intended for use with a cardiac stimulation device such as a pacemaker. Although the present invention will be described with reference to the embodiments shown in the drawings, it should be understood that the present invention can be embodied in many alternate forms or embodiments. In addition, any suitable size, shape or type of elements or materials may be used.

FIG. 1 illustrates a known pacing lead 20 designed for intravenous insertion and contact with the endocardium, and as such, may be conventionally referred to as an endocardial lead. The lead 20 is designed for intravenous insertion and contact with the endocardium and, as such, may be conventionally referred to as an endocardial lead. The lead 20 is provided with an elongated lead body 22 which includes coil or helically wound electrical conductors (not shown in this view) covered with an insulation sheath 24. The insulation sheath is preferably fabricated of silicone rubber, polyurethane or other suitable plastic. At a proximal end 26 of the pacing lead 20 is a connector assembly 28, which is provided with sealing rings 30, and which carries at least one, and preferably a pair of electrical contacts 32.

The connector assembly 28 is constructed using known techniques and is preferably fabricated of silicone rubber, polyurethane or other suitable plastic. Contacts 32 are preferably fabricated of stainless steel or other suitable electrically conductive material. The lead 20 is constructed to include a hollow interior extending from the proximal end 26 to a distal end 34. The hollow interior allows for the introduction of a stylet during implant, which is beneficial in allowing the surgeon to guide the otherwise flexible lead 20 from the point of venous insertion to the myocardium.

At the distal end 34 of the pacing lead 20 is an electrode assembly 36 which is discussed in more detail below. A suture sleeve 42, slidably mounted around lead body 22, serves to stabilize the pacing lead 20 at the site of venous insertion.

FIGS. 2 and 3 depict a known construction for the distal end 36 of the pacing lead 20 of FIG. 1. In FIGS. 2 and 3, a helical electrode 44 is affixed to an advanceable electrical interconnect 46. The electrical interconnect 46 is also electrically connected to the conductor 48 which extends from the distal end to the proximal end of the pacing lead 20. The electrical interconnect 46 thus includes a tail portion 50, to which the conductor 48 is secured, a central shaft portion 52 and a head portion 54. The helical electrode 44 is connected to the head portion 54. The central shaft portion 52 of the electrical interconnect 46 passes through a seal assembly 56. The seal assembly 56 may include a pair of retaining rings 58 which cooperate to secure a resilient ring seal 60. The seal assembly 56 prevents bodily fluids from penetrating into the axial void extending through the center of the pacing lead 20.

As also depicted in FIGS. 2 and 3, the distal end 34 of the pacing lead 20 terminates in a sleeve 62 which is essentially a cylindrical element having a central bore within which the helical electrode 44 is disposed and retractable. The sleeve 62 is preferably fabricated from a biocompatible elastomeric material. The distal tip of sleeve 62 may include one or more metallic rings 64, which are useful during implant to allow a physician to verify the position of the helical electrode 44 relative to the metallic ring 64 in either the extended or retracted position by the use of a fluoroscope. Further, the sleeve 62 includes a knob 66 extending from the inner diameter to guide the rotative advancement of the helical electrode 44. It is to be understood that techniques for implanting a pacing lead and advancing the fixation elements are known in the art, and, therefore, will not be discussed here.

The proximal end of the sleeve 62 is affixed to a stepped cylindrical element 68, which is preferably formed from a biocompatible nonconductive material. The stepped cylindrical element 68 includes a cylindrical portion 70 which slides into the proximal end of the cylindrical sleeve 62 and is bonded thereto. The seal assembly 56 is located between an end-face 72 of the stepped cylindrical element 68 and an internal step 74 of the sleeve 62.

As further illustrated in FIGS. 2 and 3, the proximal end of the distal assembly 36 may include a second ring electrode or sensor electrode 76 spaced proximally of the distal tip. The ring electrode 76 is electrically interconnected to a second conductor 78 which also extends from the proximal to the distal end of the lead body 22 and is helically wrapped about the cylindrical insulation containing the first conductor 48. The second electrical conductor 78 is also preferably encased in an insulation sleeve 80. The second electrical conductor 78 extends to and interconnects with an electrical contact (not shown) located at the connector assembly 28 at the proximal end 26 of the pacing lead 20.

In FIGS. 2 and 3, a therapeutic delivery means is provided which includes a therapeutic bullet 82 centrally disposed with respect to the helical electrode 44, that is, along the axis of the helix. The therapeutic bullet 82 is preferably secured to the head portion 54 of the electrical interconnect 46, and advanceable therewith. As depicted in FIG. 3, when the helical electrode 44 is fully extended and inserted into the myocardium upon implant, the therapeutic bullet 82 does not extend out of the end of the sleeve 62 as does the helical electrode 44. Although, according to the design illustrated in FIGS. 2 and 3, the therapeutic bullet 82 is only advanceable with the advancement of the electrical interconnect 46, other constructions are known according to which the therapeutic bullet is independently advanceable.

With the construction just described, it was earlier explained that this known thread/screw mechanism works smoothly when the helix electrode is straight and undamaged. However, the helix is susceptible to deformation due to its "delicate" strength and mishandling during assembly processes. A deformed or damaged helix will not only cause undesirable "sticky" or "jumpy" helix movement during the extension/retraction operation, but it may also disable the thread/screw mechanism. In addition, the thread/screw mechanism may be jammed by heart tissues that may become trapped inside the header. The new thread/screw mechanism described below is being developed to minimize these problems.

It was to avoid this situation that the present invention was sought.

Figure 4:
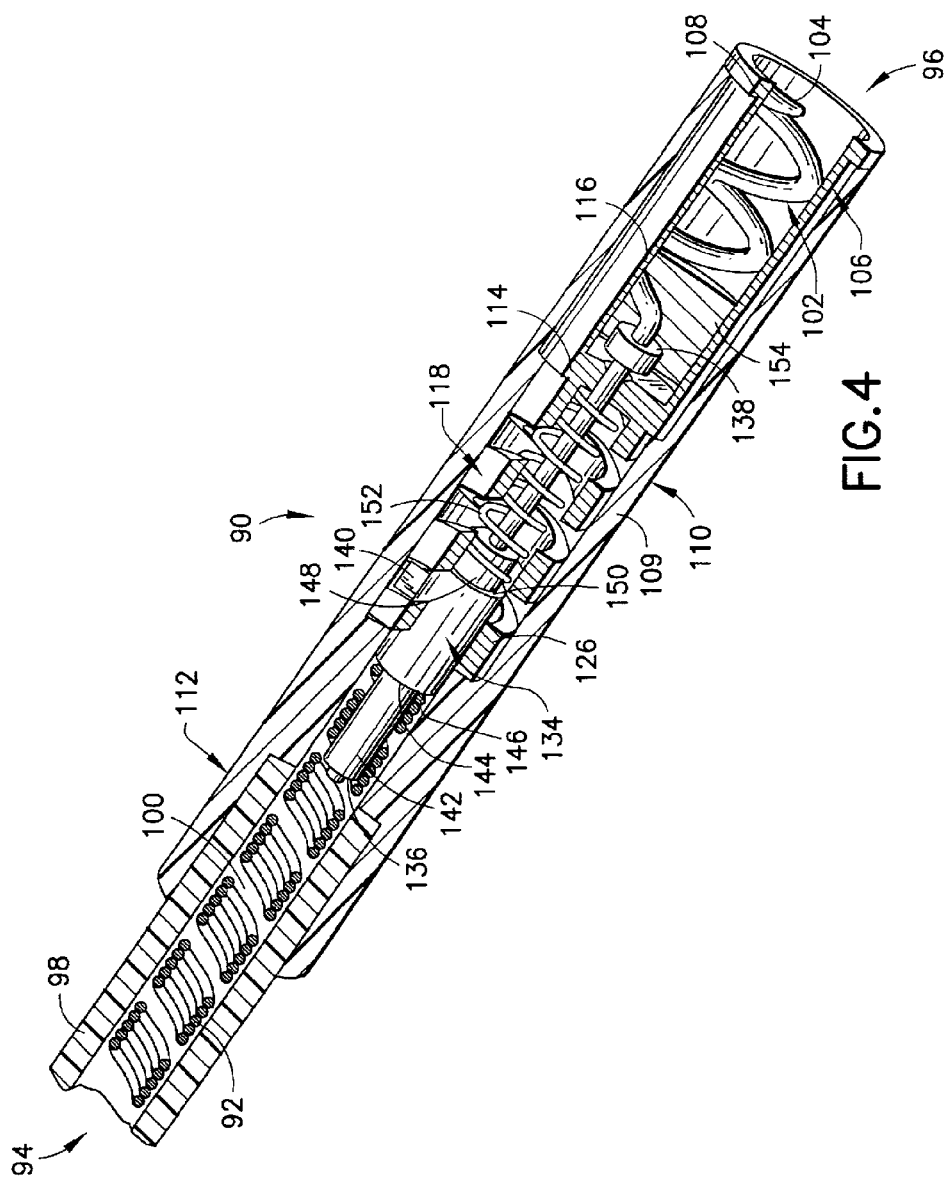
FIG. 4 is a longitudinal cross-section view of a distal end of a lead according to one embodiment and with an electrode in a retracted position.
Figure 5:
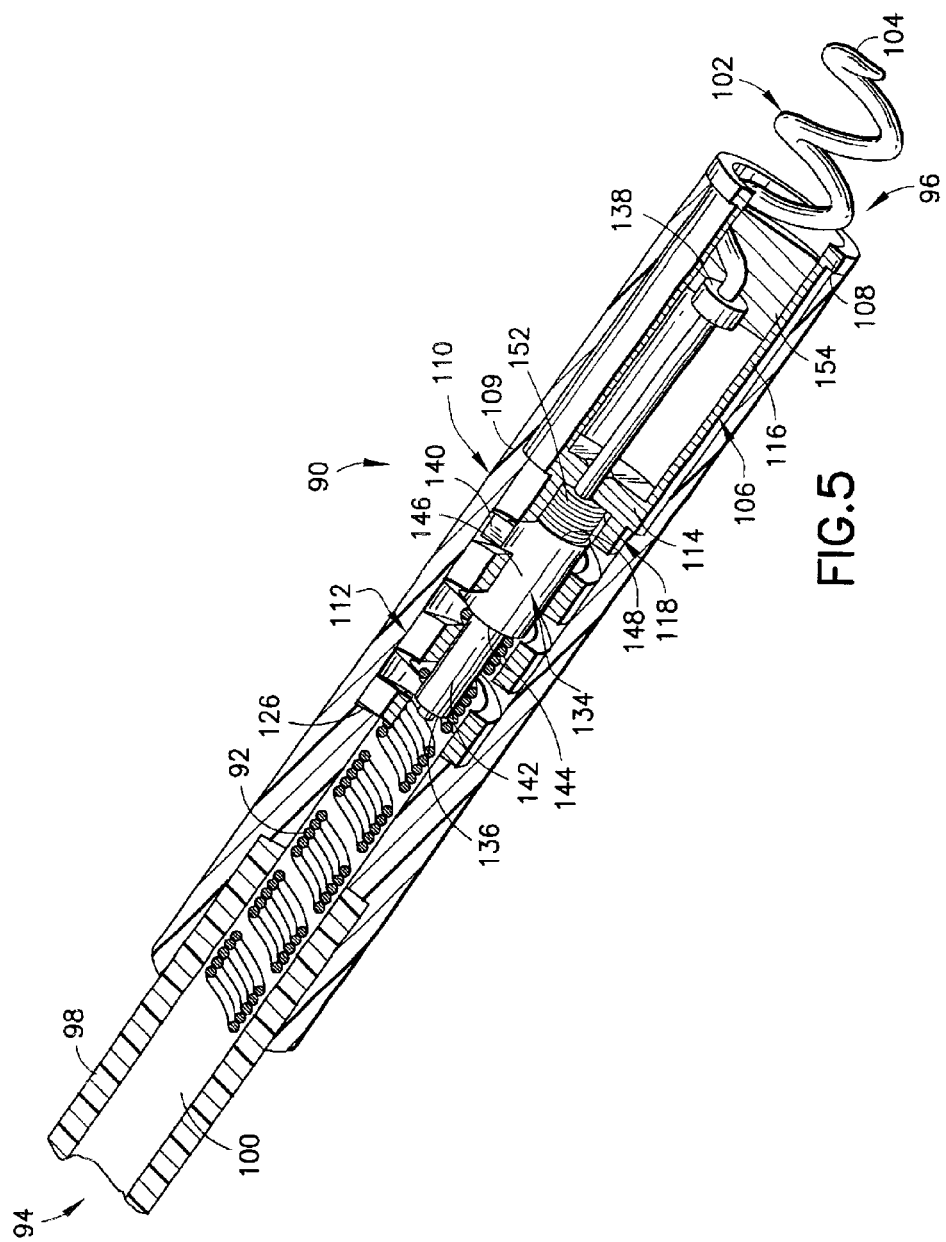
FIG. 5 is a longitudinal cross-section view similar to FIG. 4 but showing the electrode in an extended position.

Turning now to FIGS. 4 and 5, with continued reference to FIG. 1, an implantable endocardial lead 90 is illustrated which extends between proximal and distal ends (as with the lead 20) for use with a cardiac stimulation device such as a pacemaker. In this instance, an electrical conductor 92 within the lead 90 extends between proximal and distal ends generally indicated by reference numerals 94, 96, respectively. An insulation sheath 98 covers the conductor 92 and, together, the insulation sheath and the conductor define an internal chamber 100 which extends from the proximal end to the distal end of the lead 90. As in the instance of the lead 20, the lead 90 also has one or more electrical contacts 32 coupled to the proximal end of the electrical conductor 92.

In a manner to be described in more detail below, an active fixation electrode 102 is coupled to the distal end of the conductor 92. The active fixation electrode includes an electrically active helix 104 which is movable between a retracted position (FIG. 4) fully within the lead and an extended position (FIG. 5) advanced beyond the distal end of the lead for effecting penetration into the myocardial tissue. Further, the lead 90 includes an electrically active housing 106 at its distal end, terminating at an integral electrically active terminal rim 108 which is coaxial with the helix 104 at the distal end of the lead. A sleeve 109 of silicone rubber or other suitable dielectric material overlies the electrically active housing while leaving exposed the terminal rim 108. A resilient coupling mechanism 110 is provided for maintaining electrical continuity between the active fixation electrode and the electrically active housing throughout movement of the active fixation electrode between the retracted position and the extended position. Additionally, a guide system 112 located proximally of the active fixation electrode 102 is provided for rotating the electrically active helix 104 about the longitudinal axis as the helix is moved between the retracted and extended positions. These components will all be described in greater detail below.

Figure 6:
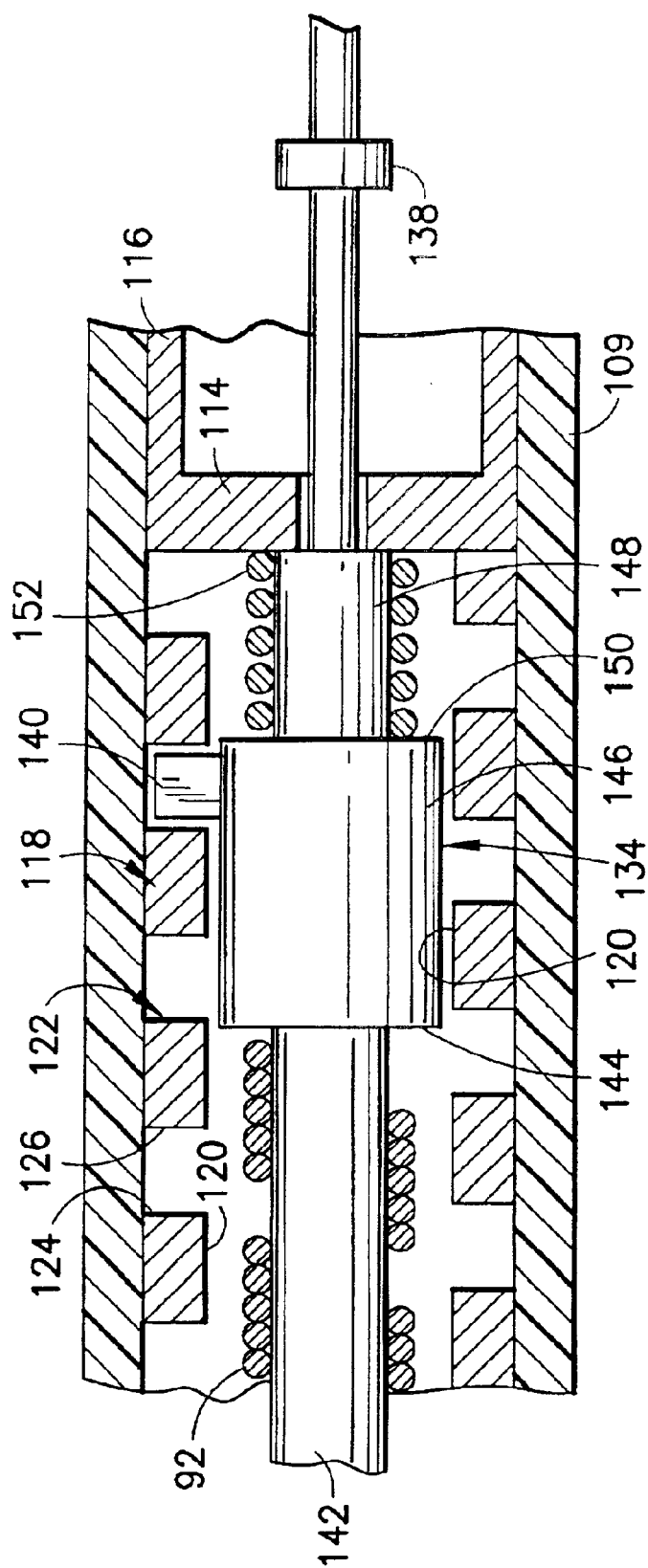
FIG. 6 is a fragmented cross-section view of a portion of the distal end of FIG. 4.
Figure 7:
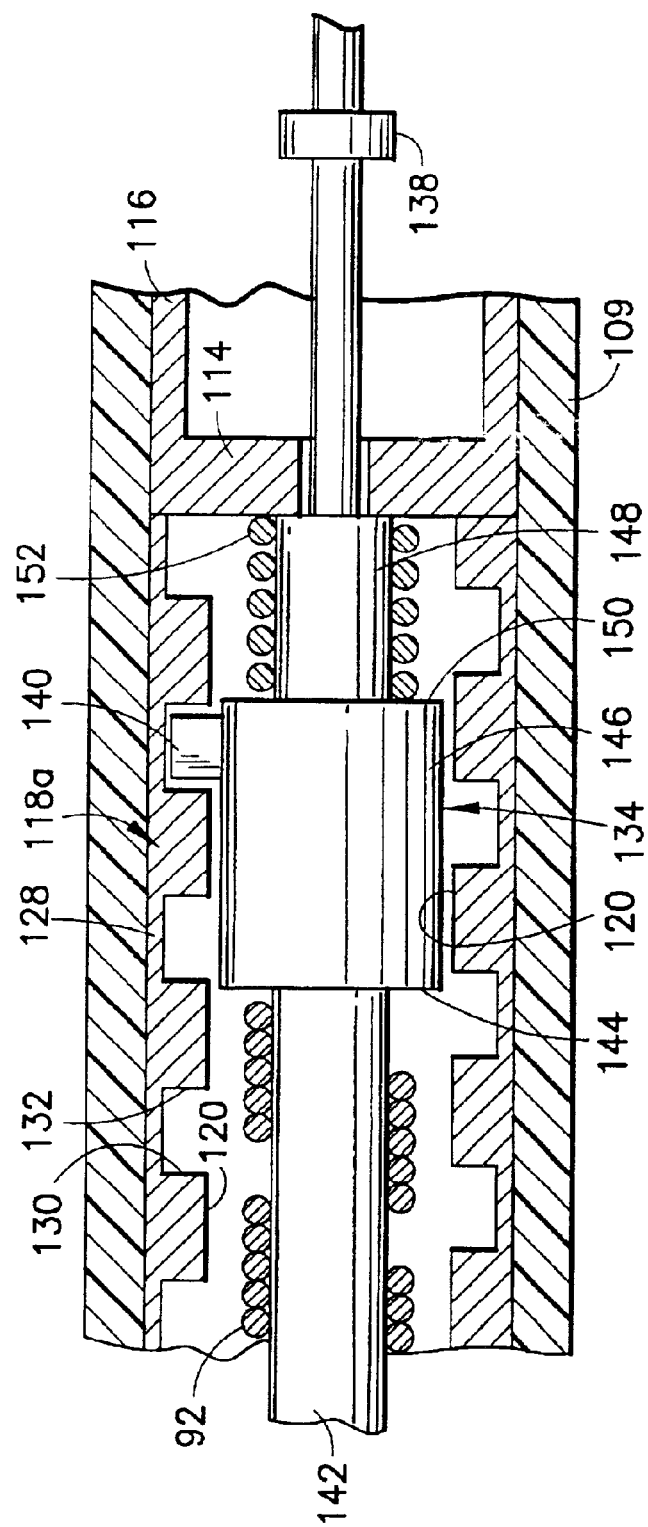
FIG. 7 is a fragmented cross-section view of a portion of the distal end of a lead according to another embodiment.

The electrically active housing 106 includes a generally planar A bulkhead member 114 extending transversely of the longitudinal axis of the lead 90, a tubular end region 116 extending away from the bulkhead member to the terminal rim 108 at the distal end of the lead. With continued reference to FIGS. 4 and 5, and with additional reference now to FIG. 6, a cylindrical guide member 118 is seen to be integral with the bulkhead member 114 and extends proximally away from the bulkhead member with an inner facing peripheral surface 120. The guide system 112 includes a spiral track member 122 (FIG. 6) formed fully into and through the inner facing peripheral surface 120 of the cylindrical guide member defined by opposed spaced parallel side walls 124, 126, the spiral track member extending proximally away from the bulkhead member to a proximal rim 126 distant from the bulkhead member. In another embodiment illustrated in FIG. 7, a modified spiral track member 118a is also defined by a bottom wall 128 connecting side walls 130, 132. This embodiment including the bottom wall 128 is a more robust construction of the guide system 112 than the FIG. 6 embodiment.

The active fixation electrode includes a conductive shaft 134 having an outer peripheral surface, a longitudinal axis generally coaxial with the electrical conductor 92, and extending between proximal and distal ends 136, 138, respectively, and has outwardly projecting follower member 140 slidably engaged with the spiral track member. The electrical conductor 92 is fixed to the proximal end 136 of the conductive shaft 134 as by being crimped onto a tail portion 142, then welded to a proximal annular shoulder 144. An annular collar 146 is integral with the conductive shaft 134 at a location intermediate the proximal and distal ends 136, 138 and projects radially from the longitudinal axis of the conductive shaft to an outer rim which lies radially beyond the outer peripheral surfaces of the conductive shaft as represented by the tail portion 142 and by a head portion 148 extending toward the distal end.

The head portion 148 is coaxial with the annular collar 146 and is smaller in diameter than the annular collar to define a distal annular shoulder 150 at its intersection with the annular collar 146. The internal peripheral surface 120 of the spiral track member 122 faces and is slidably engaged with the conductive shaft. A compression spring 152 is intermediate and engaged with the bulkhead member 114 and with the distal annular shoulder 150. The annular collar 146 is distant from the bulkhead member when the active fixation electrode 102 is in the retracted position (FIG. 4) and is proximate the bulkhead member when the active fixation electrode is in the extended position (FIG. 5), the compression spring biasing the annular collar in a direction away from the bulkhead member.

As seen in FIGS. 4 and 5, a therapeutic element 154 of known composition and generally cylindrical in shape may be provided, coaxial with and fixed on the distal end of the conductive shaft. In customary fashion, the therapeutic element is formed of a biocompatible matrix material of sufficient rigidity to penetrate the myocardial tissue.

In operation of the lead 90 to effect penetration of the helix 104 into myocardial tissue, the electrical conductor 92 is advanced in a distal direction from the proximal end of the lead. By reason of the engagement of the follower member 140 with the spiral track member 122 of the cylindrical guide member 118, the force in the distal direction is imparted to the conductive shaft 134 against the bias of the compression spring 152. The spiral track member causes the helix 104 of the active fixation electrode to rotate with the advancing movement around the longitudinal axis of the lead until the distal annular shoulder 150 is positioned proximate the bulkhead member. Withdrawal of the electrical conductor 92 in a proximal direction causes the helix 104 of the active fixation electrode to rotate with the retreating movement around the longitudinal axis of the lead until the distal annular shoulder 150 is positioned at a maximum distance from the bulkhead member.

As earlier mentioned, the spiral track member 122 of the cylindrical guide member 118 and the follower member 140 of the conductive shaft 134 are both more robust and stronger than the combination helix electrode and header thread post of earlier designs. Further, potential helix jamming problems due to the heart tissue entrapment are also minimized since the thread/screw mechanism is located in the back end of the header where it is isolated from tissue.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable endocardial lead having a longitudinal axis and extending between proximal and distal ends for use with a cardiac stimulation device, the lead comprising:

an electrical conductor within the lead extending between proximal and distal ends;

an active fixation electrode comprising an electrically active helix coaxial with the endocardial lead, coupled to the distal end of the electrical conductor, and movable between a retracted position fully within the lead and an extended position advanced beyond the distal end of the lead for effecting penetration into the myocardial tissue;

a generally planar bulkhead member extending transversely of the longitudinal axis and located proximally of the electrically active helix in the retracted position; and a guide system located proximally of the bulkhead member, the guide system comprising a spiral track member adapted to engage the active fixation electrode for rotating the electrically active helix about the longitudinal axis as the helix is moved between the retracted and extended positions.

2. An implantable endocardial lead having a longitudinal axis and extending between proximal and distal ends for use with a cardiac stimulation device, the lead comprising:

an electrically active housing comprising a tubular end region extending to a terminal rim at the distal end of the lead;

an electrical conductor within the lead extending between proximal and distal ends;

an active fixation electrode within and spaced from the electrically active housing and comprising an electrically active helix coaxial with the endocardial lead coupled to the distal end of the electrical conductor and movable between a retracted position fully within the housing and an extended position advanced beyond the terminal rim of the housing for effecting penetration into the myocardial tissue;

a generally planar bulkhead member extending transversely of the longitudinal axis and located proximally of the electrically active helix in the retracted position; and a guide system located proximally of the bulkhead member, the guide system comprising a spiral track member adapted to engage the active fixation electrode, for rotating the electrically active helix about the longitudinal axis as the helix is moved between the retracted and extended positions.

3. An implantable endocardial lead as set forth in claim 2 comprising:

an insulation sheath covering the electrical conductor, the sheath and the electrical conductor together defining an internal chamber extending from the proximal end to the distal end; and an electrical connector being coupled to the proximal end of the electrical conductor.

4. An implantable endocardial lead as set forth in claim 2 and further comprising:

a resilient coupling mechanism for maintaining electrical continuity between the active fixation electrode and the electrically active housing throughout movement of the active fixation electrode between the retracted position and the extended position.

5. An implantable endocardial lead as set forth in claim 2 wherein the active fixation electrode comprises an electrically active helix advanceable outward relative to the distal end of the conductor for effecting penetration into myocardial tissue.

6. An implantable endocardial lead as set forth in claim 2 and further comprising:

a therapeutic element integral with the active fixation electrode formed of a biocompatible matrix material being of sufficient rigidity to penetrate the myocardial tissue.

7. An implantable endocardial lead as set forth in claim 2 and further comprising:

a therapeutic element generally cylindrical in shape coaxial with and fixed on the distal end of the conductive shaft and formed of a biocompatible matrix material being of sufficient rigidity to penetrate the myocardial tissue.

8. An implantable endocardial lead as set forth in claim 2 wherein the active fixation electrode comprises an electrically active helix advanceable outward relative to the distal end of the conductor for effecting penetration into myocardial tissue; and wherein the electrically active housing comprises an electrically active collar coaxial with the helix at the distal end of the lead.

9. An implantable endocardial lead as set forth in claim 2 wherein the spiral track member of the guide system extends proximally away from the bulkhead member to a proximal rim distant from the bulkhead member; and wherein the active fixation electrode comprises a conductive shaft having an outwardly projecting follower member slidably engaged with the spiral track member, the electrical conductor being coupled to a proximal end of the conductive shaft.

10. An implantable endocardial lead as set forth in claim 9 wherein the conductive shaft comprises:

an outer peripheral surface extending between the proximal end of the conductive shaft and a distal end of the conductive shaft;

an annular collar integral with the conductive shaft intermediate the proximal and distal ends and projecting radially from the longitudinal axis to an outer rim beyond the outer surface of the conductive shaft; and a head portion coaxial with and extending distally from the annular collar and being of reduced diameter than the annular collar to define a distal annular shoulder at its intersection with the annular collar; and wherein the spiral track member has an internal peripheral surface facing and slidably engaged with a part of the conductive shaft;

a compression spring intermediate between and engaged with the bulkhead member and with the distal annular shoulder;

the annular collar being distant from the bulkhead member when the active fixation electrode is in the retracted position and being proximate the bulkhead member when the active fixation electrode is in the extended position, the compression spring biasing the annular collar in a direction away from the bulkhead member.

11. An implantable endocardial lead as set forth in claim 9 wherein the electrically active helix is fixed to a distal end of the conductive shaft.

12. An implantable endocardial lead as set forth in claim 9 wherein the guide system comprises:

a cylindrical guide member integral with and extending proximally away from the bulkhead member of the electrically active housing and having an inner facing peripheral surface; and wherein the spiral track member of the guide system is formed into the inner facing peripheral surface of the cylindrical guide member and defined by opposed spaced parallel side walls.

13. An implantable endocardial lead as set forth in claim 9 wherein the guide system comprises:

a cylindrical guide member integral with and extending proximally away from the bulkhead member of the electrically active housing and having an inner facing peripheral surface; and wherein the spiral track member of the guide system is formed into the inner facing peripheral surface of the cylindrical guide member and defined by opposed spaced parallel side walls and a bottom wall connecting the side walls.

14. An implantable endocardial lead having a longitudinal axis for use with a cardiac stimulation device, the lead comprising:

an electrical conductor within the lead, the electrical conductor having proximal and distal ends;

an electrode coupled to the distal end of the electrical conductor;

a helix coaxial with the endocardial lead and movable between a retracted position within the lead and an extended position advanced beyond a distal end of the lead for effecting penetration into myocardial tissue;

a generally planar bulkhead member extending transversely of the longitudinal axis and located proximally of the helix in the retracted position; and a guide system, located proximally of the bulkhead member, comprising a spiral track member adapted to slidably engage an outwardly projecting follower member coupled to the helix for rotating the helix about the longitudinal axis as the helix is moved between the retracted and extended positions.

15. The implantable endocardial lead as set forth in claim 14 wherein the electrode comprises an electrically active housing comprising a tubular end region extending to a terminal rim at the distal end of the lead, wherein the helix is at least partially contained within and spaced apart from the electrically active housing when in the retracted position.

16. The implantable endocardial lead as set forth in claim 14 further comprising:

a therapeutic element formed of a biocompatible matrix material being of sufficient rigidity to penetrate the myocardial tissue.

17. The implantable endocardial lead as set forth in claim 14 wherein the helix is electrically active.

18. The implantable endocardial lead as set forth in claim 17 further comprising a conductive shaft coupled between the distal end of the electrical conductor and the helix, the conductive shaft having an outwardly projecting follower member slidably engaged with the spiral track member.

19. The implantable endocardial lead as set forth in claim 14 wherein the guide system further comprises:

a cylindrical guide member having an inner facing peripheral surface, wherein the spiral track member of the guide system is formed into the inner facing peripheral surface of the cylindrical guide member and defined by opposed spaced parallel side walls.

20. The implantable endocardial lead as set forth in claim 14 further comprising:

an insulation sheath covering the electrical conductor, the sheath and the electrical conductor together defining an internal chamber extending from the proximal end to the distal end; and an electrical connector being coupled to the proximal end of the electrical conductor.

* * * * *